(12) United States Patent
Taube et al.

(10) Patent No.: US 8,974,469 B2
(45) Date of Patent: Mar. 10, 2015

(54) SNARE

(75) Inventors: Andris Taube, Gainesville, FL (US);
Matthew M. Quest, Bothell, WA (US);
Sophie Marcoux, Gainesville, FL (US)

(73) Assignee: Medical Device Technologies, Inc., Gainesville, FL (US)

(*) Notice: Subject to any disclaimer, the term of this patent is extended or adjusted under 35 U.S.C. 154(b) by 0 days.

(21) Appl. No.: 12/765,574

(22) Filed: Apr. 22, 2010

(65) Prior Publication Data

US 2011/0264106 A1    Oct. 27, 2011

(51) Int. Cl.
*A61B 17/221* (2006.01)
*A61B 17/22* (2006.01)

(52) U.S. Cl.
CPC ......... *A61B 17/221* (2013.01); *A61B 17/22031* (2013.01); *A61B 2017/22035* (2013.01); *A61B 2017/2212* (2013.01); *A61B 2017/2215* (2013.01)
USPC ....................................... 606/113

(58) Field of Classification Search
USPC .......... 606/108, 110, 113, 114, 127, 159, 200
See application file for complete search history.

(56) References Cited

U.S. PATENT DOCUMENTS

| | | | |
|---|---|---|---|
| 3,955,578 A | 5/1976 | Chamness et al. | |
| 4,425,908 A | 1/1984 | Simon | |
| 5,057,114 A | 10/1991 | Wittich et al. | |
| 5,064,428 A | 11/1991 | Cope et al. | |
| 5,098,440 A | 3/1992 | Hillstead | |
| 5,133,733 A | 7/1992 | Rasmussen | |
| 5,171,233 A | 12/1992 | Amplatz et al. | |
| 5,562,678 A | 10/1996 | Booker | |
| 5,658,296 A | 8/1997 | Bates et al. | |
| 5,697,936 A | 12/1997 | Shipko et al. | |
| 5,720,754 A | 2/1998 | Middleman et al. | |
| 5,725,552 A | 3/1998 | Kotula et al. | |
| 6,066,149 A | 5/2000 | Samson et al. | |
| 6,077,274 A * | 6/2000 | Ouchi et al. | 606/113 |
| 6,086,577 A | 7/2000 | Ken et al. | |
| 6,099,534 A | 8/2000 | Bates et al. | |
| 6,156,055 A | 12/2000 | Ravenscroft | |
| 6,159,220 A | 12/2000 | Gobron et al. | |
| 6,174,318 B1 | 1/2001 | Bates et al. | |
| 6,217,589 B1 | 4/2001 | McAlister | |
| 6,224,612 B1 | 5/2001 | Bates et al. | |
| 6,280,451 B1 | 8/2001 | Bates et al. | |
| 6,348,056 B1 | 2/2002 | Bates et al. | |
| 6,458,139 B1 | 10/2002 | Palmer et al. | |

(Continued)

FOREIGN PATENT DOCUMENTS

WO    PCTUS0005996    9/2000

*Primary Examiner* — Kathleen Holwerda
*Assistant Examiner* — Sarah W Aleman
(74) *Attorney, Agent, or Firm* — IpHorgan Ltd.

(57) ABSTRACT

A snare for snaring an article in a vessel of a vascular system or other body vessel. The snare includes a core cable having a proximal end portion and a distal end portion. The snare also includes first, second and third loops each having a proximal end portion and a distal end portion, and a mid-portion therebetween formed by spaced apart first and second sides connected together at the distal end portion of the loop. The mid-portions of each of the loops cross over mid portions of one of the other two loops, and the loops are only connected together at their proximal end portions, where they are gathered together and attached to the distal end portion of the core cable. The loops are movable between an open position and a closed position.

22 Claims, 4 Drawing Sheets

(56) References Cited

U.S. PATENT DOCUMENTS

| | | |
|---|---|---|
| 6,458,145 B1 * | 10/2002 | Ravenscroft et al. ......... 606/200 |
| 6,500,182 B2 | 12/2002 | Foster |
| 6,520,968 B2 | 2/2003 | Bates et al. |
| 6,527,781 B2 | 3/2003 | Bates et al. |
| 6,544,279 B1 | 4/2003 | Hopkins et al. |
| 6,558,404 B2 | 5/2003 | Tsukernik |
| 6,624,612 B1 | 9/2003 | Lundquist |
| 6,626,915 B2 * | 9/2003 | Leveillee ...................... 606/114 |
| 6,663,651 B2 | 12/2003 | Krolic et al. |
| 6,942,673 B2 | 9/2005 | Bates et al. |
| 7,011,681 B2 | 3/2006 | Vesely |
| 7,041,116 B2 | 5/2006 | Goto et al. |
| 7,169,154 B1 | 1/2007 | Que et al. |
| 7,282,055 B2 * | 10/2007 | Tsuruta .......................... 606/127 |
| 7,776,052 B2 * | 8/2010 | Greenberg et al. ............ 606/108 |
| 2004/0243174 A1 | 12/2004 | Ackerman et al. |
| 2005/0049612 A1 | 3/2005 | Urbanski et al. |
| 2007/0106304 A1 | 5/2007 | Hammack et al. |
| 2007/0118165 A1 * | 5/2007 | DeMello et al. ............... 606/159 |
| 2008/0086149 A1 | 4/2008 | Diamant et al. |
| 2009/0069828 A1 * | 3/2009 | Martin et al. ................. 606/159 |

* cited by examiner

SNARE

BACKGROUND

Various instruments are used for removing foreign objects from the body of a patient. For example, such instruments may be used for removal of stones such as kidney stones, gallstones, and the like from various sites along the urinary tract of a patient's body. Retrieval devices are also widely used for removing foreign articles from the vascular system of a patient. In such cases, examples of the foreign articles include vascular stents, vena cava filters, and parts of medical devices such as catheters, guide wires, cardiac leads, or the like, which may break and become detached during medical procedures or need removal for other reasons.

Some types of these instruments employ a collapsible wire basket arranged within a flexible catheter formed as a tubular sheath adapted to penetrate body passages to reach the location where the object is to be evacuated. Another known type of retrieval device for use within a body vessel is a "snare" configured as one or more distal loops which, in operation, may be positioned over a free end of the foreign body, and which may be collapsed and tightened around the foreign body so that it may be retrieved.

DETAILED DESCRIPTION

Figure 1:
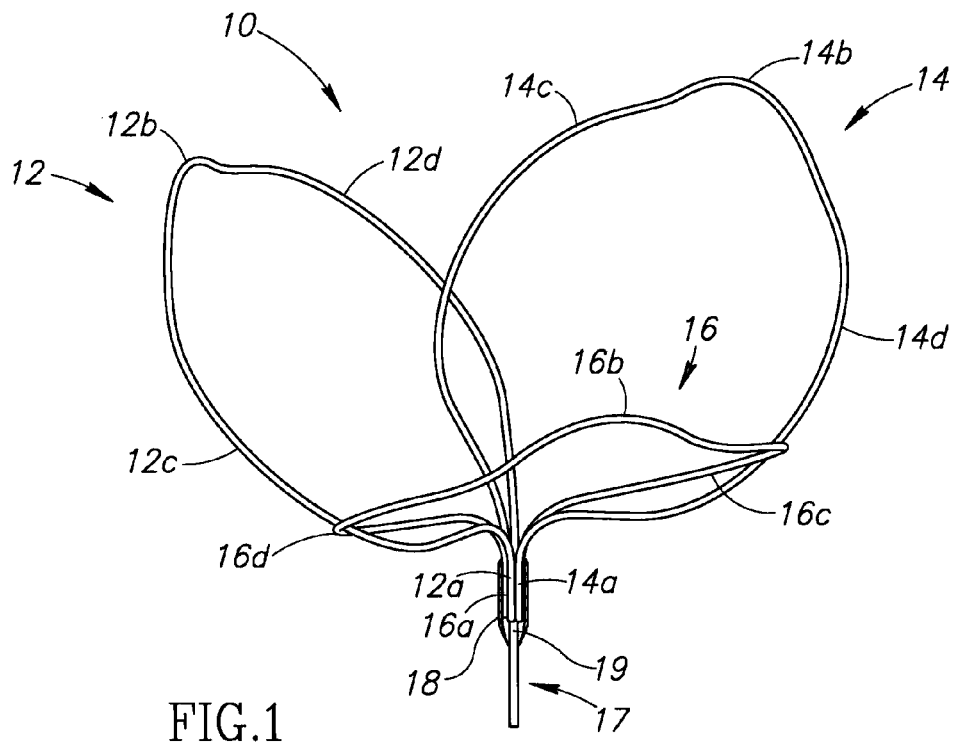
FIG. 1 is a top perspective view of one embodiment of an intravascular snare.
Figure 2:
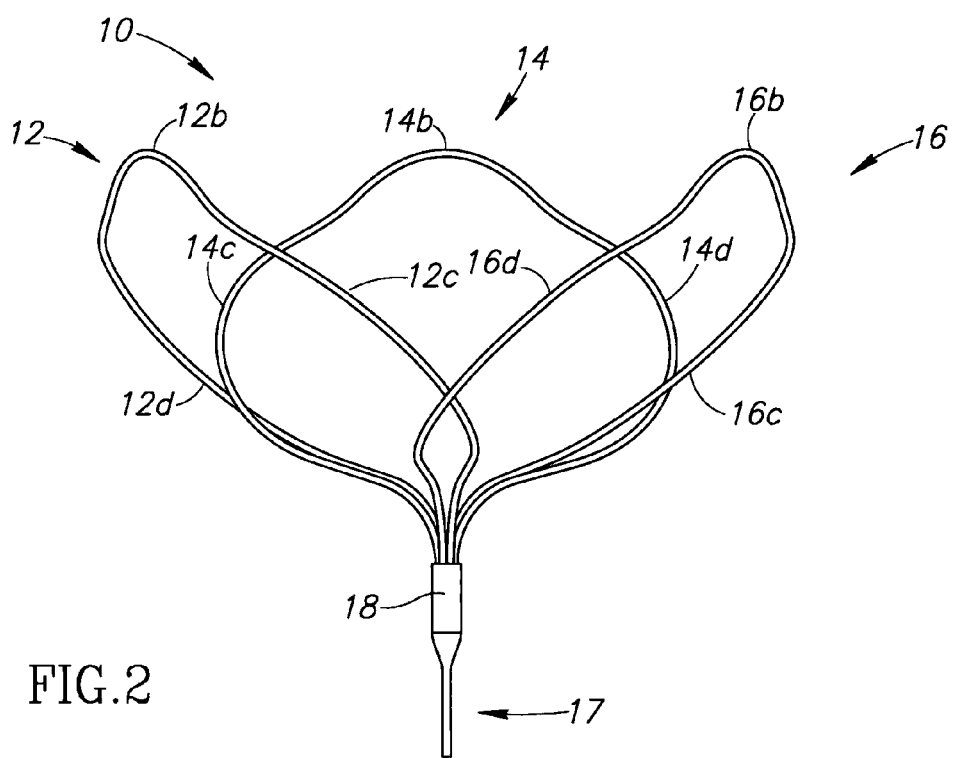
FIG. 2 is a side view of the intravascular snare shown in FIG. 1.

An intravascular snare 10 according to one embodiment is shown in FIGS. 1 and 2. The snare 10 includes a first loop 12, a second loop 14, and a third loop 16 that are each coupled to a core cable 17 (or "core wire") having a proximal end portion and a distal end portion 19. More specifically, each of the loops 12, 14, and 16 includes a proximal end portion 12a, 14a, and 16a, respectively, that are gathered together and coupled to the distal end portion 19 of the core cable 17. Further, each of the loops 12, 14, and 16 includes a distal end portion 12b, 14b, and 16b, respectively, spaced away from and positioned forward of the corresponding proximal end portion 12a, 14a, and 16a of the loop. Each of the loops 12, 14, and 16 also includes a mid-portion 12d, 14d, and 16d, respectively, on a first side and a mid-portion 12c, 14c, and 16c, respectively, on a spaced-apart second side of the loop spaced between the proximal end portion 12a, 14a, and 16a and the distal end portion 12b, 14b, and 16b, respectively, of the loop.

Each of the loops 12, 14, and 16 may be formed from a solid or multi-strand material. In some embodiments the loops 12, 14, and 16 are formed from a multi-strand composite of nitinol wire and platinum wire (e.g., five strands of nitinol wire and two strands of platinum wire) so that the platinum wire provides radiopacity while the nitinol wire provides shape memory and/or superelastic characteristics. The multiple strands forming the loops 12, 14, and 16 may be braided, knitted, woven, wound, or the like. As can be appreciated, other material(s) may be used for the loops 12, 14, and 16 as well.

The proximal end portions 12a, 14a, and 16a of the loops 12, 14, and 16 may be fixedly coupled to the distal end portion 19 of the core cable 17 by a soldering process. Further, a stainless steel ferrule 18 may be crimped over the solder joint connecting the proximal end portions 12a, 14a, and 16a of the loops 12, 14, and 16 to the distal end portion 19 of the core cable 17 to provide a secure connection. In some embodiments, the core cable 17 may be formed from a solid strand of nitinol wire, but the core cable may also be formed from other materials and/or multiple strands of one or more materials. The core cable 17 may also be tapered at the distal end 19 to reduce the resulting cross-sectional area of the coupling region between the core cable 17 and the loops 12, 14, and 16. Additionally, the core cable 17 may be formed by rearward extension of the wires forming the loops 12, 14, and 16, thus eliminating the need to solder the loops 12, 14, and 16 to a separate core cable.

Figure 6:
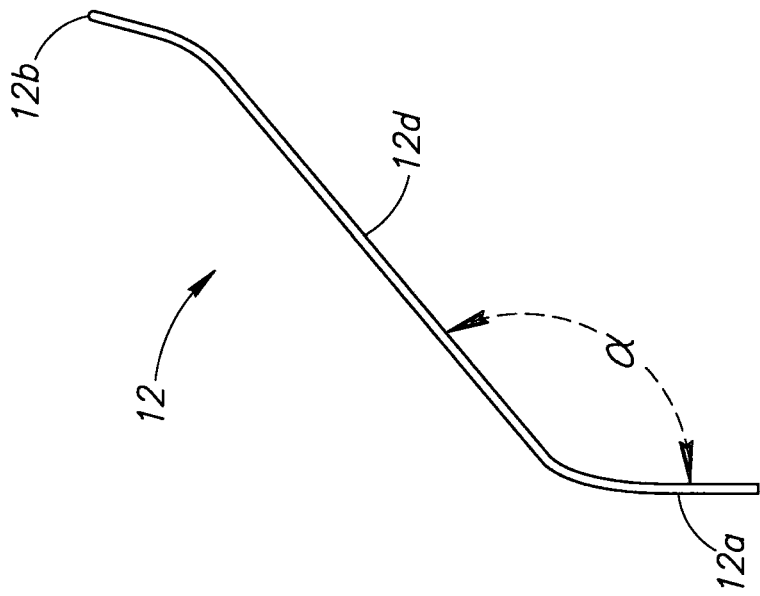
FIG. 6 is a side elevational view of one loop of the intravascular snare shown in FIGS. 1 and 2.
Figure 5:
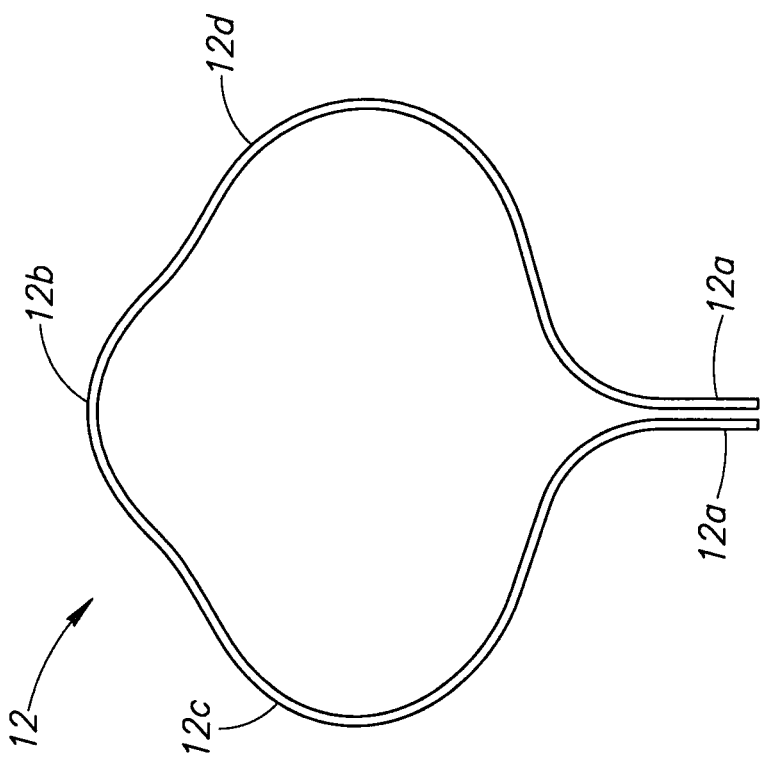
FIG. 5 is a front elevational view of one loop of the intravascular snare shown in FIGS. 1 and 2.

For each of the loops 12, 14, and 16, the distal end portion 12b, 14b, and 16b, respectively, is positioned forward of the proximal end portion 12a, 14a, and 16a, respectively, and the mid-portion extends laterally outwardly relative to the distal end 19 of the core cable 17. Further, the distal end portion of each of the loops 12, 14, and 16 curve forwardly away from the mid-portions thereof. The specific shape of the loops 12, 14, and 16 may best be viewed in FIGS. 5 and 6, which illustrate a front view (FIG. 5) and a side view (FIG. 6) of the first loop 12, which is representative of the second loop 14 and the third loop 16. As shown in FIG. 6, the mid-portion 12d, as well as the mid-portion 12c, of the loop 12 extends laterally outward from the proximal end portion 12a at an angle α. Preferably, the angle α is between about 90 and 150 degrees (e.g., 130 degrees), but it is not so limited. Further, when viewed from the side as in FIG. 6, the distal end portion 12b curves forwardly away from the mid-portion 12d (and mid-portion 12c). As best seen in FIG. 5, the distal end portion 12b has an arcuate shape that forms what may be referred to as a "ski tip." The "ski tip" shape of the distal end portions 12b, 14b and 16b may help guide the loops 12, 14, and 16 forward during advancement in a body vessel, thereby reducing the likelihood that the loops will bend backward during advancement causing the snare to have a diminished effectiveness. That is, the "ski tip" deflects against the walls of a body vessel which allows the distal end portions 12b, 14b and 16b to slide along the walls during advancement and prevents "digging" into the walls. As discussed below with reference to FIGS. 7 and 8, the shape and configuration of the loops 12, 14, and 16 provide a snare that is effectively functional to capture articles (e.g., stents, filters, medical components, or the like) positioned within a vessel of a vascular system or other body vessel. In this example, the loops 12, 14, and 16 are substantially identical in size and shape, however, it will be appreciated that different numbers, sizes, and shapes may be used for the loops of a snare.

Figure 3:
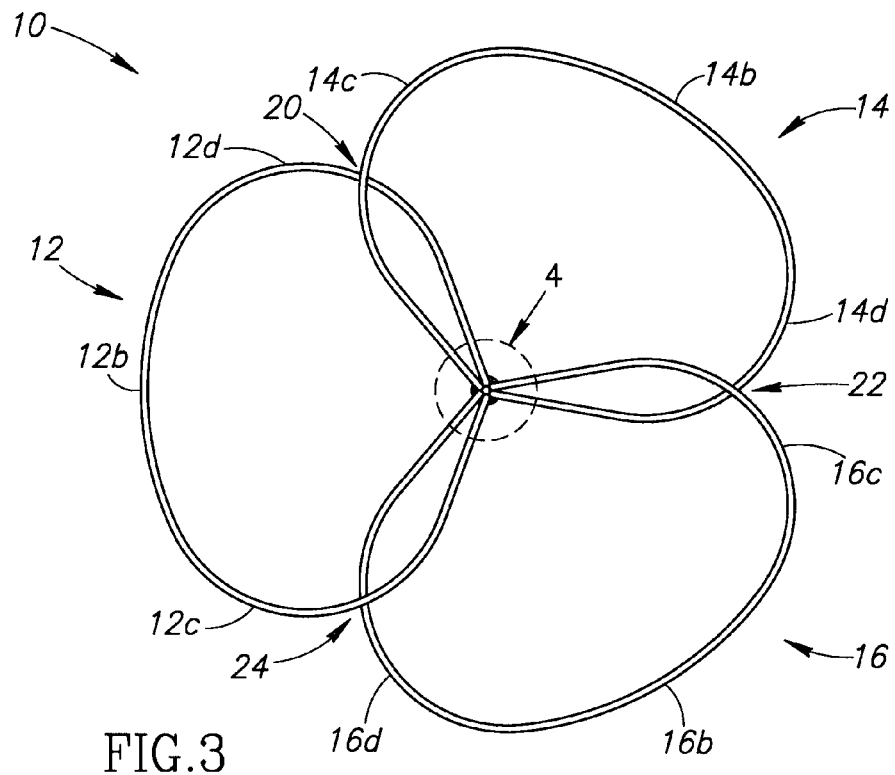
FIG. 3 is a top view of the intravascular snare shown in FIGS. 1 and 2.
Figure 4:
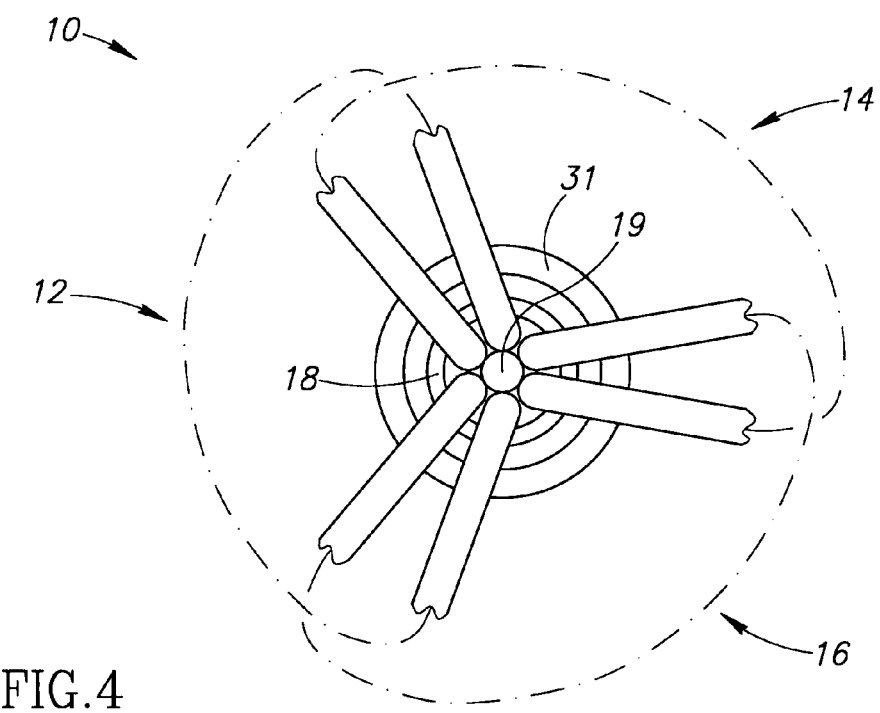
FIG. 4 is a detail view of a portion indicated by dashed circle 4 of FIG. 3.

FIG. 3 illustrates a top view of the intravascular snare 10 shown in FIGS. 1 and 2, and FIG. 4 illustrates a detail view of the portion of FIG. 3 indicated by the dashed circle 4. As shown in FIG. 3, the mid-portion 12d (the first side) of the first loop 12 and the mid-portion 14c (the second side) of the second loop 14 are arranged with one crossing over each other (when viewed as shown in FIG. 3) at a crossover point 20, with the mid-portion 14c being inward of the mid-portion 12d. Further, the mid-portion 14d (the first side) of the second loop 14 and the mid-portion 16c (the second side) of the third loop 16 are arranged with one crossing over each other at a crossover point 22, with the mid-portion 16c being inward of the mid-portion 14d. Similarly, the mid-portion 16d (the first side) of the third loop 16 and the mid-portion 12c (the second side) of the first loop 12 are arranged with one crossing over each other at a crossover point 24, with the mid-portion 12c being inward of the mid-portion 16d. In this example, each of the crossover points 20, 22, and 24 are positioned at a location away from the proximal end portions of each of the respective loops 12, 14, and 16 by about 40-60 percent of the length of the total distance between the proximal end portion and the distal end portion thereof. As can be appreciated, the specific locations of the crossover points 20, 22, and 24 as well as the degree of overlap between the loops 12, 14, and 16 may be selected dependent on a particular application.

Further, it is noted that the loops 12, 14, and 16 are not connected to each other at the crossover points 20, 22, and 24, or elsewhere except at their proximal end portions. This feature permits each of the loops 12, 14, and 16 to move independently of each other, thereby improving the ability of the snare 10 to capture articles in a vessel of a vascular system or other body vessel. Further, this feature includes a manufacturing and/or cost advantage over designs that include interlaced or connected loops by not including complex connection points.

The configuration in the illustrated embodiment for the gathering of the proximal end portions 12a, 14a and 16a of the loops 12, 14, and 16, respectively, at the distal end 19 of the core cable 17 may best be viewed in FIG. 4. As can be appreciated, the proximal end portions of the loops 12, 14, and 16 around the circumference of the distal end 19 of the core cable 17 are positioned to produce the overlapping feature such that the crossover points 20, 22, and 24 are provided. It is noted that the dashed lines shown in FIG. 4 are provided to show the positioning of the proximal end portions 12a, 14a and 16a of the loops 12, 14, and 16, respectively, and do not represent a particular shape for the loops 12, 14, and 16.

Figure 7:
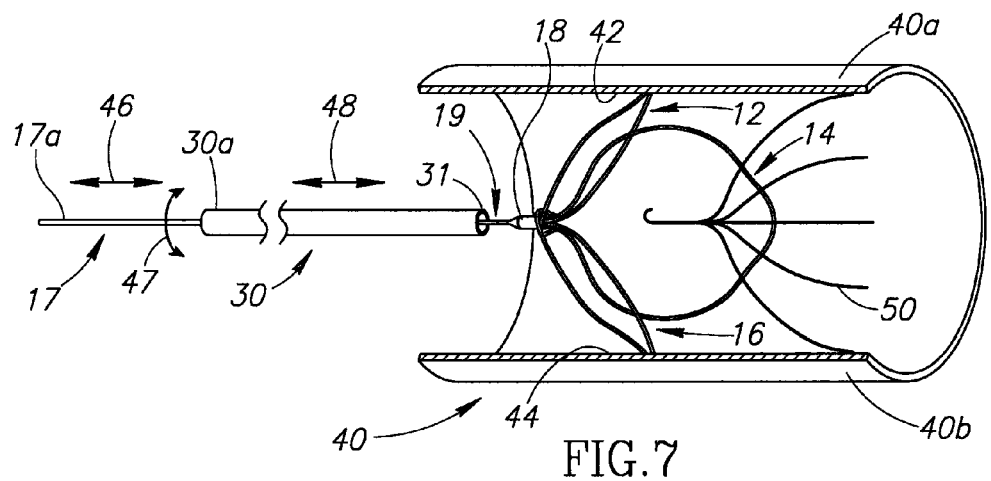
FIG. 7 is a side perspective view of the intravascular snare shown in FIGS. 1 and 2 in an open position during operation in a vessel of a vascular system.
Figure 8:
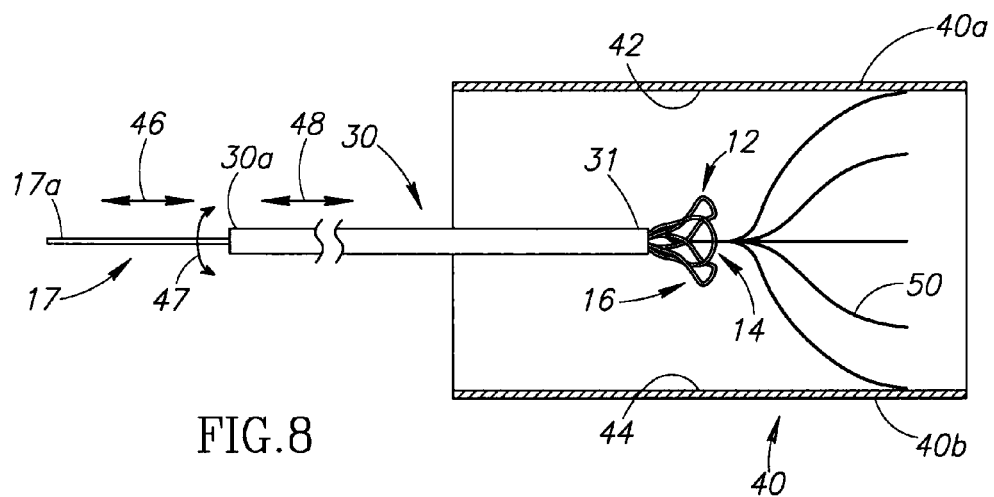
FIG. 8 is a side view of the intravascular snare shown in FIGS. 1 and 2 in a partially closed position during operation in a vessel of a vascular system.

FIG. 4 also shows a distal end 31 of an elongate sheath 30 (shown in FIGS. 7 and 8). The sheath 30 may be sized to receive the core cable 17 and the loops 12, 14, and 16 when the loops are inserted or retracted into the sheath. Further, the sheath 30 is operative to be inserted into a vessel of a vascular system or other body vessel so that a portion of the vessel may be accessed by the intravascular snare 10. The sheath 30 may be any suitable length, such as 100 centimeters, 200 centimeters, or other length. The sheath 30 may comprise a special or generic flexible catheter formed from any suitable material, such as polyvinyl chloride (PVC), flouropolymer, polyurethane with a hydrophilic coating, or other biocompatible material.

Figure 9:
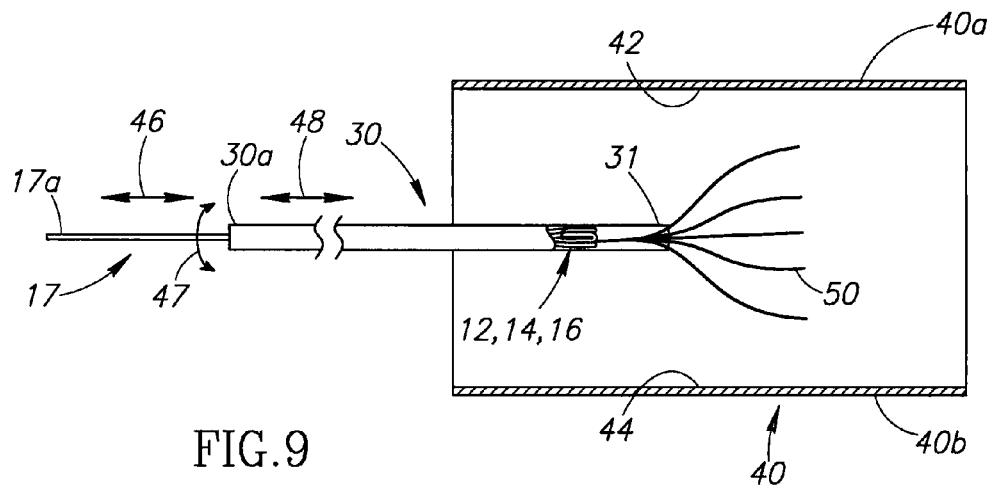
FIG. 9 is a side view of the intravascular snare shown in FIGS. 1 and 2 in a fully closed position during operation in a vessel of a vascular system.

FIGS. 7, 8 and 9 illustrate the operation of the intravascular snare 10 inside a vessel 40 of a vascular system. In this example, the sheath 30 may be introduced percutaneously into a vessel (e.g., the femoral artery). The sheath 30 may be injected with radio-opaque dye or otherwise include a radio-opaque marker that can be seen on live X-ray or fluoroscopy so that it may be guided to a position of the vessel 40 where the snare 10 is to be used to retrieve a vena cava filter 50 or other article inside the vessel. As shown in FIG. 7, the loops 12, 14, and 16 extend outwardly from the distal end portion 31 of the sheath 30. This position of the snare 10 relative to the sheath 30 may generally be referred to as the "open position." In the open position, the loops 12, 14, and 16 extend laterally outwardly with their distal end portions in an open position and define a space therebetween for receiving at least a portion of the article therein. When in the open position, preferably the distal end portion 12b of the loop 12 contacts a first wall portion 40a of the vessel 40 at a point 42. Similarly, the distal end portion 16b of the loop 16 contacts a second wall portion 40b of the vessel 40 at a point 44, and the distal end portion 14b of the loop 14 contacts a third wall portion (not shown) of the vessel 40. The force exerted on the wall portions is generally not sufficient to deform the wall portions. As can be appreciated, the shape of the loops 12, 14, and 16 when in the open position may allow for a "sledding effect" along the walls of the vessel 40 which enable the snare 10 to capture articles positioned at or near the walls.

In operation, a user may selectively manipulate the position of the core cable 17 relative to the sheath 30 to move the snare 10 between the open position (FIG. 7), a partially closed position (FIG. 8), and a fully closed or collapsed position (FIG. 9). Such positioning of the core cable 17 and the sheath 30 relative to each other may involve moving the core cable 17 rearward or forward (as indicated by arrow 46), moving the sheath 30 rearward or forward (as indicated by arrow 48), or both. In the partially closed position, the loops 12, 14, and 16 are positioned laterally inwardly from their open position with their distal end portions 12b, 14b, and 16b in a closed position sufficiently closer together than when in the open position to grasp between one or more of the loops 12, 14, and 16 at least a portion of the vena cava filter 50 in the space. This manipulation is illustrated by the arrows 46 and 48 shown in FIGS. 7 and 8, respectively, near a proximal end 17a of the core cable 17 and a proximal end 30a of the sheath 30. In the open position, the loops 12, 14, and 16 may have substantially the shape shown in FIGS. 1-6, depending on the inner diameter of the vessel 40. As a user adjusts the position of the core cable 17 relative to the sheath 30, the loops are pulled toward and into the distal end 31 of the sheath 30 causing them to move inward and collapse in on each other as shown in FIG. 8 until the loops are fully collapsed together as shown in FIG. 9. As can be appreciated, by selectively transitioning the loops 12, 14, and 16 between the open position and the closed position, a user may retrieve articles such as the vena cava filter 50 positioned inside the vessel 40. Further, the arcuate distal ends 12b, 14b, and 16b of the loops 12, 14, 16 arc laterally inwardly as the loops 12, 14, and 16 are moved into the closed position, thereby further increasing the ability of the snare 10 to retrieve articles.

In addition to manipulating the position of the core cable 17 and the sheath 30 relative to each other as indicated by the arrows 46 and 48, the core cable 17 (and therefore the loops 12, 14, and 16) may be rotated by a user in a clockwise or counterclockwise direction (as indicated by arrow 47). As can be appreciated, rotating the core cable 17 clockwise may have a tendency to glide the loops 12, 14, and 16 along the wall of the vessel 40, and rotating the core cable 17 counterclockwise may help drive the loops 12, 14, and 16 toward the side wall and help to grab articles adjacent to the wall of the vessel 40.

The foregoing embodiments described herein depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

While particular embodiments have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A snare for snaring an article, comprising: a core cable having a proximal end portion and a circumference at a distal end portion; and first, second and third loops, each of the first, second and third loops having a proximal end portion and a distal end portion, and a mid-portion therebetween, and being formed by spaced apart first and second sides connected together at the distal end portion of the loop, the distal end portions being positioned forward of the proximal end portions, the first side of the first loop and the second side of the second loop being arranged with one crossing over the other at a first crossover point and being disconnected, the first side of the second loop and the second side of the third loop being arranged with one crossing over the other at a second crossover point and being disconnected, and the first side of the third loop and the second side of the first loop being arranged with one crossing over the other at a third crossover point and being disconnected, wherein the second side of the second loop is positioned inward of the first side of the first loop at the first crossover point, and wherein the second side of the third loop is positioned inward of the first side of the second loop at the second crossover point, and wherein the second side of the first loop is positioned inward of the first side of the third loop at the third crossover point, the distal end portions of the first, second and third loops being disconnected from each other, the proximal end portions of the first, second and third loops each comprising two proximal ends, each proximal end being directly coupled to and positioned around the circumference of the distal end portion of the core cable such that the two proximal ends of the first loop are separated from one another by one proximal end of the second loop and one proximal end of the third loop, the two proximal ends of the second loop are separated from one another by a proximal end of the first loop and a proximal end of the third loop, and the two proximal ends of the third loop are separated from one another by a proximal end of the first loop and a proximal end of the second loop, the first, second and third loops being movable between an open position whereat the first, second and third loops extend laterally outwardly with their distal end portions in an open position and define a space therebetween for receiving at least a portion of the article therein, and a collapsed position whereat the first, second and third loops are positioned laterally inwardly from their open position with their distal end portions in a closed position closer together than when in the open position, and the mid-portions of the first, second and third loops being disconnected from each other to permit independent movement of each as the first, second and third loops are moved between the open and closed positions, wherein the distal end portion of each of the first, second and third loops has an arcuate shape, the first, second and third loops when in the open position extend laterally outwardly and forward with the mid-portions of the first, second and third loops at an angle ranging from 90 to approximately 120 degrees relative to the distal end portion of the core cable, and the distal end portion of each of the first, second and third loops curves in the direction of the core cable.

2. The snare of claim 1, wherein the first side of the first loop and the second side of the second loop cross over the other at a location away from the proximal end portion of each by about 40-60 percent of the length of the total distance between the proximal end portion and the distal end portion thereof, first side of the second loop and the second side of the third loop cross over the other at a location away from the proximal end portion of each by about 40-60 percent of the length of the total distance between the proximal end portion and the distal end portion thereof, and the first side of the third loop and the second side of the first loop cross over the other at a location away from the proximal end portion of each by about 40-60 percent of the length of the total distance between the proximal end portion and the distal end portion thereof.

3. The snare of claim 1, wherein the first, second and third loops each have substantially the same length from its proximal end portion to its distal end portion.

4. The snare of claim 1, wherein the first, second and third loops each has at least one of a shape memory and a superelastic characteristic.

5. The snare of claim 1, wherein each of the first, second and third loops is formed from multiple strands of material.

6. The snare of claim 1, further comprising: an elongate sheath adapted to penetrate into a body vessel and sized to receive the core cable and the first, second and third loops, the elongate sheath including a distal end having an opening such that the first, second and third loops may be retracted within the sheath and protracted therefrom by selectively manipulating the proximal end portion of the core cable relative to the sheath.

7. The snare of claim 1, wherein each of the first, second and third loops includes a material that provides radiopacity.

8. The snare of claim 1, wherein each of the first, second and third loops is formed from multiple strands of nitinol wire.

9. The snare of claim 1, wherein each of the first, second and third loops is formed from multiple strands of wires including nitinol wire and wire comprising radiopaque material.

10. The snare of claim 1, wherein each of the first, second and third loops is attached to the core cable by solder.

11. The snare of claim 1, wherein each of the first, second and third loops is attached to the core cable by a crimped ferrule.

12. The snare of claim 1, wherein the core cable is formed from a nitinol wire that is tapered near the distal end portion of the core cable.

13. The snare of claim 1, wherein the first, second and third loops have substantially identical shapes.

14. The snare of claim 1, wherein the first, second and third loops when in the open position extend laterally outwardly and forward with the mid-portions of the first, second and third loops at an angle of about 120 degrees relative to the distal end portion of the core cable.

15. A snare for snaring an article, comprising: first, second and third loops, each of the first, second and third loops having a proximal end portion and a distal end portion, and a mid-portion therebetween, and being formed by spaced apart first and second sides connected together at the distal end portion of the loop, the distal end portions being positioned forward of the proximal end portions, the first side of the first loop and the second side of the second loop being arranged with one crossing over the other and being disconnected, the first side of the second loop and the second side of the third loop being arranged with one crossing over the other and being disconnected, and the first side of the third loop and the second side of the first loop being arranged with one crossing over the other and being disconnected, wherein the second side of the second loop is positioned inward of the first side of the first loop, and wherein the second side of the third loop is positioned inward of the first side of the second loop, and wherein the second side of the first loop is positioned inward of the first side of the third loop, the distal end portions of the first, second and third loops being disconnected from each other, the proximal end portions of the first, second and third loops each comprising two proximal ends, each proximal end being directly coupled to and positioned around the circumference of the distal end portion of the core cable such that the two proximal ends of the first loop are separated from one another by one proximal end of the second loop and one proximal end of the third loop, the two proximal ends of the second loop are separated from one another by a proximal end of the first loop and a proximal end of the third loop, and the two proximal ends of the third loop are separated from one another by a proximal end of the first loop and a proximal end of the second loop, the first, second and third loops being movable between an open position whereat the first, second and third loops extend laterally outwardly with their distal end portions in an open position and define a space therebetween for receiving at least a portion of the article therein, and a collapsed position whereat the first, second and third loops are positioned laterally inwardly from their open position with their distal end portions in a closed position closer together than when in the open position, and the mid-portions of the first, second and third loops being disconnected from each other to permit independent movement of each as the first, second and third loops are moved between the open and closed positions, wherein the distal end portion of each of the first, second and third loops has an arcuate shape, the first, second and third loops when in the open position extend laterally outwardly and forward with the mid-portions of the first, second and third loops at an angle ranging from 90 to approximately 120 degrees relative to the distal end portion of the core cable, and the distal end portion of each of the first, second and third loops curves in the direction of the core cable.

16. The snare of claim 15, further comprising: a core cable having a proximal end portion and a distal end portion, wherein the proximal end portions of the first, second and third loops are gathered together and attached to the distal end portion of the core cable.

17. A snare for snaring an article, comprising: a core cable having a proximal end portion and a distal end portion; and first, second and third loops formed from material including nitinol wire, each of the first, second and third loops having a proximal end portion and a distal end portion, and a mid-portion therebetween, and being formed by spaced apart first and second sides connected together at the distal end portion of the loop, the distal end portions being positioned forward of the proximal end portions and being curved forwardly away from the mid-portions thereof, the first side of the first loop and the second side of the second loop being arranged with one crossing over the other and being disconnected, the first side of the second loop and the second side of the third loop being arranged with one crossing over the other and being disconnected, and the first side of the third loop and the second side of the first loop being arranged with one crossing over the other and being disconnected, the distal end portions of the first, second and third loops being disconnected from each other, wherein the second side of the second loop is positioned inward of the first side of the first loop, and wherein the second side of the third loop is positioned inward of the first side of the second loop, and wherein the second side of the first loop is positioned inward of the first side of the third loop, the proximal end portions of the first, second and third loops each comprising two proximal ends, each proximal end being directly coupled to and positioned around the circumference of the distal end portion of the core cable such that the two proximal ends of the first loop are separated from one another by one proximal end of the second loop and one proximal end of the third loop, the two proximal ends of the second loop are separated from one another by a proximal end of the first loop and a proximal end of the third loop, and the two proximal ends of the third loop are separated from one another by a proximal end of the first loop and a proximal end of the second loop, the first, second and third loops being movable between an open position whereat the first, second and third loops extend laterally outwardly with their distal end portions in an open position and define a space therebetween for receiving at least a portion of the article therein, and a collapsed position whereat the first, second and third loops are positioned laterally inwardly from their open position with their distal end portions in a closed position closer together than when in the open position for grasping between at least one of the first, second and third loops the portion of the article in the space, and the mid-portions of the first, second and third loops being disconnected from each other to permit independent movement of each as the first, second and third loops are moved between the open and closed positions, wherein the distal end portion of each of the first, second and third loops has an arcuate shape, and the first, second and third loops when in the open position extend laterally outwardly and forward with the mid-portions of the first, second and third loops at an angle ranging from 90 to approximately 120 degrees relative to the distal end portion of the core cable.

18. A snare for snaring an article, comprising: first, second and third cables, each of the first, second and third cables having a first portion, second portion and a loop portion spaced between the first portion and the second portion, each of the first, second, and third loop portions having a proximal end portion and a distal end portion, and a mid-portion therebetween, and being formed by spaced apart first and second sides connected together at the distal end portion of the loop portion, the distal end portions being positioned forward of the proximal end portions, the first side of the first loop portion and the second side of the second loop portion being arranged with one crossing over the other and being disconnected, the first side of the second loop portion and the second side of the third loop portion being arranged with one crossing over the other and being disconnected, and the first side of the third loop portion and the second side of the first loop portion being arranged with one crossing over the other and being disconnected, wherein the second side of the second loop is positioned inward of the first side of the first loop, and wherein the second side of the third loop is positioned inward of the first side of the second loop, and wherein the second side of the first loop is positioned inward of the first side of the third loop, the distal end portions of the first, second and third loop portions being disconnected from each other, the proximal end portions of the first, second and third loops each comprising two proximal ends, each proximal end being directly coupled to and positioned around the circumference of the distal end portion of the core cable such that the two proximal ends of the first loop are separated from one another by one proximal end of the second loop and one proximal end of the third loop, the two proximal ends of the second loop are separated from one another by a proximal end of the first loop and a proximal end of the third loop, and the two proximal ends of the third loop are separated from one another by a proximal end of the first loop and a proximal end of the second loop, the first, second and third loop portions being movable between an open position whereat the first, second and third loop portions extend laterally outwardly with their distal end portions in an open position and define a space therebetween for receiving at least a portion of the article therein, and a collapsed position whereat the first, second and third loop portions are positioned laterally inwardly from their open position with their distal end portions in a closed position closer together than when in the open position, and the mid-portions of the first, second and third loop portions being disconnected from each other to permit independent movement of each as the first, second and third loop portions are moved between the open and closed positions, wherein the distal end portion of each of the first, second and third loops has an arcuate shape, and the first, second and third loops when in the open position extend laterally outwardly and forward with the mid-portions of the first, second and third loops at an angle ranging from 90 to approximately 120 degrees relative to the distal end portion of the core cable.

19. A method for snaring an article inside a body vessel, comprising: inserting a snare into the body vessel, the snare comprising: a core cable having a proximal end portion and a distal end portion; first, second and third loops, each of the first, second and third loops having a proximal end portion and a distal end portion, and a mid-portion therebetween, and being formed by spaced apart first and second sides connected together at the distal end portion of the loop, the distal end portions being positioned forward of the proximal end portions, the first side of the first loop and the second side of the second loop being arranged with one crossing over the other and being disconnected, the first side of the second loop and the second side of the third loop being arranged with one crossing over the other and being disconnected, and the first side of the third loop and the second side of the first loop being arranged with one crossing over the other and being disconnected, the distal end portions of the first, second and third loops being disconnected from each other, the proximal end portions of the first, second and third loops each comprising two proximal ends, each proximal end being directly coupled to and positioned around the circumference of the distal end portion of the core cable such that the two proximal ends of the first loop are separated from one another by one proximal end of the second loop and one proximal end of the third loop, the two proximal ends of the second loop are separated from one another by a proximal end of the first loop and a proximal end of the third loop, and the two proximal ends of the third loop are separated from one another by a proximal end of the first loop and a proximal end of the second loop, wherein the second side of the second loop is positioned inward of the first side of the first loop, and wherein the second side of the third loop is positioned inward of the first side of the second loop, and wherein the second side of the first loop is positioned inward of the first side of the third loop, the first, second and third loops being movable between an open position whereat the first, second and third loops extend laterally outwardly with their distal end portions in an open position and define a space therebetween for receiving at least a portion of the article therein, and a collapsed position whereat the first, second and third loops are positioned laterally inwardly from their open position with their distal end portions in a closed position closer together than when in the open position, and the mid-portions of the first, second and third loops being disconnected from each other to permit independent movement of each as the first, second and third loops are moved between the open and closed positions, wherein the distal end portion of each of the first, second and third loops has an arcuate shape, the first, second and third loops when in the open position extend laterally outwardly and forward with the mid-portions of the first, second and third loops at an angle ranging from 90 to approximately 120 degrees relative to the distal end portion of the core cable, and the distal end portion of each of the first, second and third loops curves in the direction of the core cable; and an elongate sheath adapted to penetrate into a body vessel and sized to receive the first, second and third loops, the elongate sheath including a proximal end and a distal end having a distal end opening; selectively manipulating at least one of the proximal end of the core cable and the proximal end of the elongate sheath to selectively retract the first, second and third loops within the distal end opening and to selectively protract the first, second and third loops from the distal end opening.

20. The method of claim 19, further comprising: selectively rotating the proximal end of the core cable relative to the elongate sheath to effect a rotation of the first, second and third loops.

21. The method of claim 20, wherein selectively rotating the proximal end of the core cable relative to the elongate sheath includes rotating in one of clockwise and counterclockwise directions to move the first, second and third loops outward toward a wall of the body vessel, and rotating the other of clockwise and counterclockwise directions to move the first, second and third loops inward away from a wall of the body vessel.

22. The method of claim 19, further comprising: advancing the snare in a forward direction through the body vessel such that the distal end portion of each of the first, second and third loops slide along walls of the body vessel.

* * * * *